United States Patent [19]

Mersch

[11] Patent Number: 5,120,979
[45] Date of Patent: Jun. 9, 1992

[54] APPARATUS AND METHOD FOR ANALYSIS OF A SAMPLE MEDIUM IN A GAP BETWEEN A TUBE AND A FLOAT

[75] Inventor: Steven H. Mersch, Germantown, Ohio

[73] Assignee: Becton, Dickinson and Company, Franklin Lakes, N.J.

[21] Appl. No.: 673,997

[22] Filed: Mar. 25, 1991

[51] Int. Cl.⁵ ................... G01N 21/86; G01N 21/00
[52] U.S. Cl. ................................ 250/574; 356/339
[58] Field of Search ............... 250/574, 560, 577; 356/382, 339

[56] References Cited

U.S. PATENT DOCUMENTS

| | | | |
|---|---|---|---|
| 3,901,602 | 8/1975 | Gravatt | 250/574 |
| 4,265,538 | 5/1981 | Wertheimer | 356/336 |
| 4,567,373 | 1/1986 | O'Meara et al. | 250/573 |
| 4,676,641 | 6/1987 | Bott | 356/338 |
| 4,771,181 | 9/1988 | Hayashi | 250/560 |
| 4,859,861 | 8/1989 | Mersch | 250/560 |
| 4,920,275 | 4/1990 | Itoh | 250/574 |
| 4,990,795 | 2/1991 | Suzuki et al. | 250/574 |
| 5,008,556 | 4/1991 | Mersch | 250/560 |

Primary Examiner—Bruce C. Anderson
Attorney, Agent, or Firm—Aaron Passman

[57] ABSTRACT

An apparatus or method identifies and quantifies components of a sample medium filling a gap of an assembly of a transparent tube and a cylindrical float located substantially coaxially with the tube. This identification or quantification is made based on the high angle scatter and/or fluorescence of the medium. A polarized monochromatic or biochromatic light beam of the wavelength for which the tube is transparent projects through an optical focusing and/or scanning system to illuminate a section of the gap with a line of light positioned parallel to the longitudinal axis of the tube but displaced laterally therefrom. Means position and rotate the tube about its longitudinal axis producing a complete circumferential illumination of the sample medium sections in the gap. Light filtering and detecting means normal to the illumination axis detects high angle light scattering properties and/or fluorescence properties from the sample medium. Signal processing means analyzes the output from the detecting means to identify and quantify the sample medium.

13 Claims, 6 Drawing Sheets

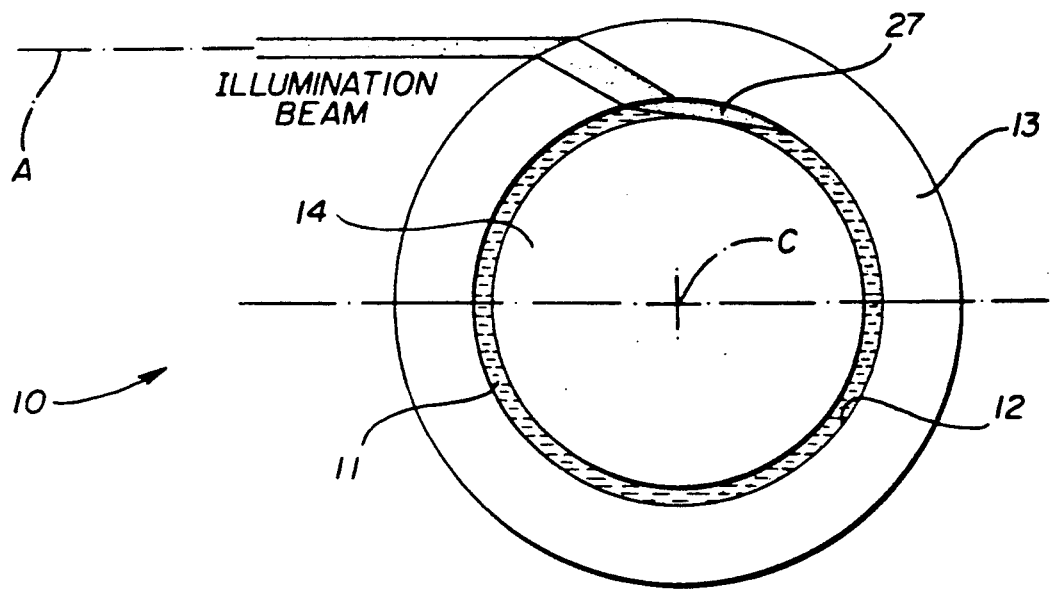
FIG-2 ILLUMINATING THE MEDIUM OCCUPYING THE GAP
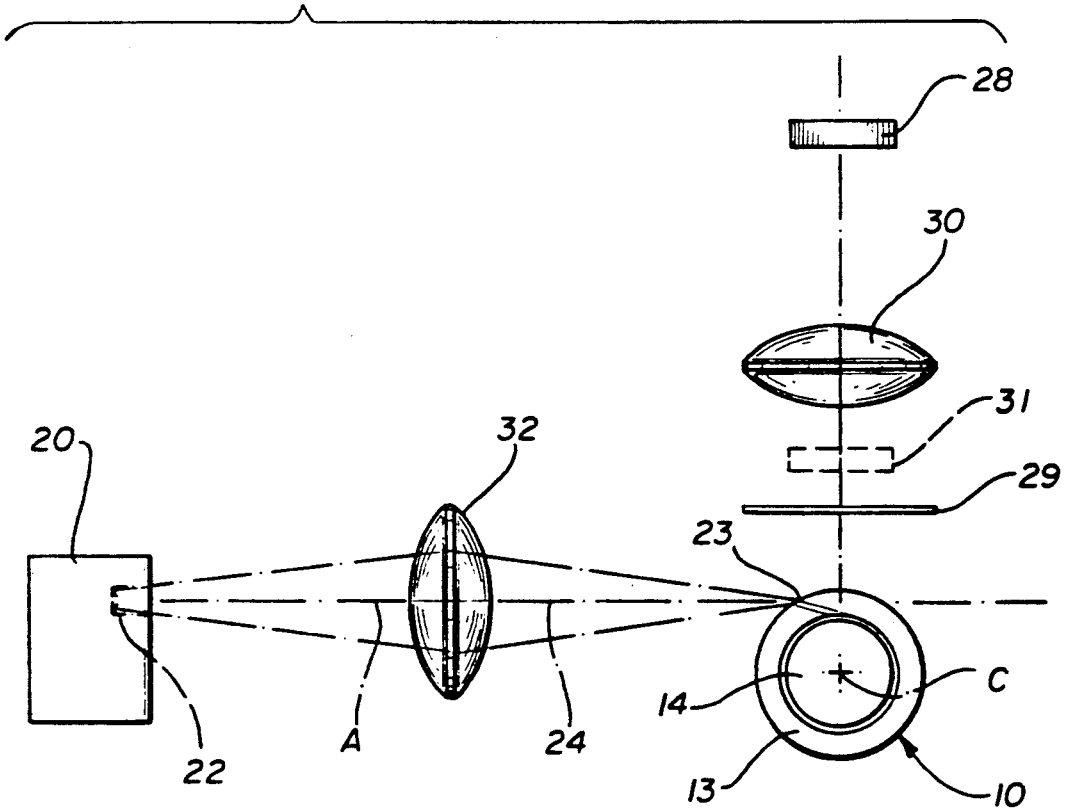
FIG-3

FIG-6 RESULTS USING SCANNED BEAM AND SINGLE ELEMENT DETECTOR IN THE NEAR FIELD.

OPTICAL LAYOUT OPTIONS

APPARATUS AND METHOD FOR ANALYSIS OF A SAMPLE MEDIUM IN A GAP BETWEEN A TUBE AND A FLOAT

FIELD OF THE INVENTION

The present invention relates to an apparatus and a method for detecting and interpreting optical properties of light passing through a sample medium occupying a gap in an assembly of a transparent tube and a cylindrical float located substantially coaxially within the tube. It also concerns the relationship between light from a polarized beam of monochromatic light aimed normal to an axis of the tube to pass through the tube so optical properties of the sample medium within the gap may be detected and analyzed.

BACKGROUND

Using light to automatically analyze or measure a contained sample without physically contacting the sample has been accomplished in cytometry, spectrophotometry, fluorometry and nephelometry. The instruments used to make such measurements and/or analysis are particularly adapted to the sample considered and the specific technique of measurement. The various techniques are well known and are mentioned herein as background relative to the particular apparatus and method disclosed and claimed.

Cytometry evaluates particles or cells passing in a stream through light one at a time and for a brief period of time. Typically five thousand particles or cells pass through the light per second and produce a signal each time the light is interrupted by the passage of a cell or particle. The signals represent scatter or fluorescent emissions. The signals are analyzed with a photomultiplier tube.

Spectrometry identifies a compound by its spectrum as produced by illuminating the compound. Spectrophotometers measure transmittance or reflectance to study those properties of specimens as a function of wavelength. Spectradiometers measure the radiant energy from a source at each wavelength throughout the spectrum. The spectral regions are separated either by calibrated filters or a calibrated monochromator. The detector receives energy from a photomultiplier.

Nephelometric turbidity is an empirical measurement of the light-scattering characteristics (Tyndall effect) of a sample of particulate matter. Intensity of scattered light at ninety degrees to the incident beam of light is measured and numerical values are obtained by comparison with the light-scattering characteristics of a known or an arbitrarily chosen material in an equivalent optical system. Comparison may also be made between transmitted light effect and scattered light effect.

Spectrochemical (spectrographic, spectrometric, spectroscopic) analysis is the determination of the chemical elements in a sample quantitatively or semi-quantitatively, by measurements of the wavelength and intensity of spectral lines produced by suitable excitation procedures with a suitable optical dispersion device. The field of spectroanalysis may be subdivided into atomic emission or absorption, molecular emission or absorption, X ray, flame, fluorescent, and other types of instrumental analysis.

Measurement of the dimensions of the components of a sample medium held within a gap between a transparent tube and a cylindrical float is a diagnostic technique used for purposes of analyzing blood samples in a quantitative buffy coat centrifugal analyzer. A particular diagnostic instrument is called QBC ®, and is sold by Becton Dickinson and Company, Franklin Lakes, N.J. That instrument includes a capillary tube containing a solid cylindrical plastic float. A patient's blood, the sample medium, is drawn into the tube, the tube end is sealed with a plastic cap and the tube spun in a microhematocrit centrifuge for five minutes. During centrifugation the plastic float having a specific gravity that is midway between that of the plasma and the red blood cells floats on top of the red blood cells and is surrounded by the expanded buffy coat. The float occupies more than 90% of the cross-sectional area of the tube and so the buffy coat is expanded ten-fold in the gap between the inside wall of the tube and the outside diameter of the float. The individual buffy coat layers have been easily measured but not automatically analyzed in a rapid manner by the technique disclosed herein. U.S. Pat. Nos. 4,567,754 and 4,190,328 disclose quantitative buffy coat tubes and the background in each patent is instructive on the slow procedures currently used to read buffy coat. Those background and disclosures are incorporated herein by reference.

The expansion of the sample medium in the gap between the bore of the capillary tube and the float is important in that the relative quantity of each component in the sample medium is a function of the gap volume or radial dimension. Therefore, the identical dimensions of each tube and float used when analyzing buffy coat is a concern.

U.S. Pat. No. 4,859,861 addresses optical techniques for measuring the bore diameter to high accuracy, allowing manufacture of tubing of a known bore. U.S. patent application Ser. No. 194,614, addresses an optical technique to directly measure the gap in a prepared QBC sample. In a fast, high accuracy, automatic QBC analyzer, it would be valuable to be able to simultaneously read the buffy coat and measure the gap dimension. This disclosure answers the need to give a fast, accurate, and automatic reading of the sample medium inside the gap formed between a precision bore capillary and its float therein, while simultaneously allowing practice of a U.S. patent application Ser. No. 194,614 U.S. Pat. No. 4,359,861.

SUMMARY OF THE INVENTION

An apparatus determines the optical properties of a sample medium within a gap in an assembly of a transparent tube and cylindrical float located substantially concentrically within the tube. The apparatus preferably has a monochromatic light or bichromatic source providing a polarized light beam along an optical axis at wavelengths for which the materials of the tube are transparent and the major axis of polarization of the light beam is normal to the longitudinal axis of the tube. A light beam controlling means converts the light beam to a line of light in a plane positioned along an axis of the tube. The tube may be aligned with the optical axis to receive the polarized light beam. Means for positioning and rotating the assembly of the tube and the cylindrical float within the plane with the line of light parallel to the longitudinal axis of the assembly and displaced laterally from the longitudinal axis of the tube illuminates a longitudinal section of the sample medium within the gap between the tube and the float. The means for positioning and rotating the assembly is most preferably capable of illuminating all radial sections of the sample medium.

A light detection means may be positioned normal to the optical axis of the light source, parallel to the longitudinal axis of the tube and aligned to receive light passing through the longitudinal section of the sample medium. A light filtering means located between the tube and the light detection means may be arranged to selectively pass an optical property indicative of the nature of the sample medium to be analyzed. Signal processing means associated with the detector analyzes signals therefrom.

The monochromatic or bichromatic light source is most preferably a laser diode or frequency doubled laser diode providing the light beam polarized normal to the longitudinal axis and along the optical axis. If a frequency doubled diode is used, the beam is bichromatic because the fundamental and frequency doubled wavelengths would both be present in the beam. The laser diode may emit light of a wavelength to cause fluorescence emissions from the medium within the tube. The light filter means may have selectable polarization filters to selectively pass light of the desired polarization of high angle scatter properties to the light detecting means. The light filter means might have selectable color filters to selectively pass light of the desired fluorescent wavelength properties to the light detecting means.

The light detecting means may include an imaging lens to form an image of the tube on a detector thereof. The detector may be a linear detector array. The signal processing means analyzes the pixels of the linear detector array to arrive at a reading of the buffy coat.

The illumination line may be formed by scanning means and the light detection means may be a single detector element placed in the near field of the sample medium or alternately in an image plane as previously described. The signal processing means would then analyze the output from the detector as a function of time to arrive at a reading of the buffy coat.

A method determines the optical properties of a sample medium within a gap of an assembly of a tube and cylindrical float located substantially concentrically within the tube. The method may have the steps of transmitting a polarized monochromatic or bichromatic light beam along an optical axis at a wavelength for which the material of the tube is transparent. The major axis of polarization of the light beam may be positioned normal to the longitudinal axis of the tube. Converting the light beam to a line of light in a plane along the axis of the tube when the tube is aligned with the optical axis to receive the polarized beam of light may be another step of the preferred method. The step of rotating and positioning an assembly of the tube and the cylindrical float within the plane of the line of light with the line of light parallel to the longitudinal axis of the assembly and displaced laterally from the longitudinal axis thereof illuminates a longitudinal section of the sample medium within the gap between the tube and the float. All radial sections of the sample medium may be illuminated over a period of time by rotating the assembly about its axis and within the line of light.

Detecting with a light detection means positioned normal to the optical axis of the light beam and parallel to the longitudinal axis of the tube and aligned to receive the light effected by the optical properties of the sample medium is another step of the method. The steps of filtering the light effected to selectively pass light indicative of the nature of the sample medium being analyzed with the light detection means and signalling the nature of the sample medium as a function of the effected light preferably follow.

BRIEF DESCRIPTION OF THE DRAWINGS

FIG. 2 shows a light ray tracing of the illumination of the sample medium occupying a gap between a tube and a float assembly in cross section and schematic form.

FIG. 3 is a top view an optical layout showing the preferred elements which illuminate the gap between the float and tube during analysis of a sample medium therein.

DETAILED DESCRIPTION OF THE DRAWINGS

Figure 1:
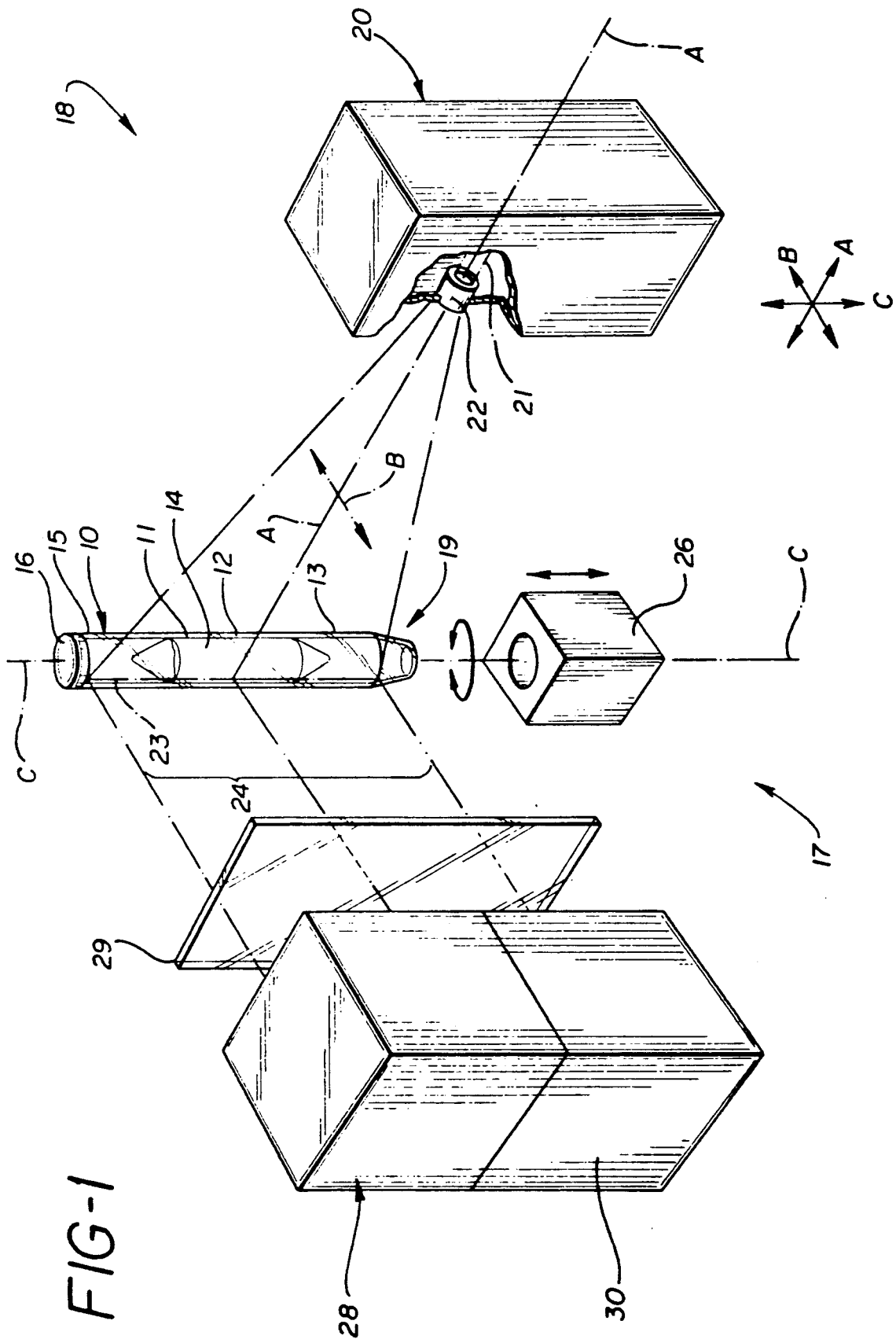
FIG. 1 is a perspective view of the basic elements in schematic form of the preferred embodiment of the apparatus to determine the optical properties of a sample medium within a gap in an assembly of a transparent tube and cylindrical float located substantially concentrically within the tube.

While this invention is satisfied by embodiments in many different forms, there is shown in the drawings and will herein be described in detail, a preferred embodiment of the invention and alternate optical layout options, with the understanding that the present disclosure is to be considered as exemplary of the principles of the invention and is not intended to limit the invention to the embodiments illustrated. The scope of the invention will be measured by the appended claims and their equivalents.

QBC ®, a product 10 sold by Becton Dickinson and Company, Franklin Lakes, N.J., is used to analyze a sample medium 11 such as venous blood captured in a thin layer within a gap 12 between a tube 13 and a float 14 within the tube 13. In a particular test to analyze human blood, a patient's blood sample is placed into the tube 13, a tube end 15 is sealed with a plastic cap 16 and the tube 13, float and sample medium 11 blood spun in a microhematocrit. During centrifugation the plastic float 14 having a specific gravity that is midway between that of the plasma and the red blood cells floats on top of the red blood cells and is surrounded by the expanded buffy coat. Since the float 14 occupies more than 90% of the cross-sectional area of the tube, see FIG. 2, the buffy coat is in the gap 12 and forms a thin layer that expands ten times. The axial length of the individual buffy coat layers can be easily measured manually but automatic measurement of the sample medium 11 as presented in this disclosure would eliminate human errors and interpretation while performing the measurement in a precise, very rapid, and economical manner.

FIG. 1 is a perspective view showing schematically the basic elements of a preferred embodiment 17 of an apparatus 18 to determine the optical properties of the sample medium 11 within the gap 12 in an assembly 19 of the transparent tube 13 and the cylindrical float 14 located substantially concentrically within the tube 13. The apparatus 18 has a monochromatic or bichromatic light source 20 providing a polarized light beam 21 along an optical axis A. The light source 20 is at wavelengths for which the materials of the tube 13 are transparent and the major axis B of polarization of the light beam 21 is normal to the longitudinal axis C of the tube 13, as best shown in FIG. 3.

In FIG. 1 a light beam controlling means 22 converts the light beam 21 to a line of light 23 in a plane 24 positioned along the axis C of the tube 13. The plane 24 also includes the optical axis A. The major axis B of polarization of the light beam is perpendicular to the plane 24. The tube 13 is aligned with the optical axis A to receive the polarized light beam 21.

A means for positioning and rotating 26 the assembly 19 of the tube 13 and the cylindrical float 14 locates the assembly 19 as shown in FIGS. 1 and 3 within the plane 24 of the line of light 23 so the line of light 23 is parallel to the longitudinal axis of the assembly 19 and is displaced laterally from the longitudinal axis C. The line of light 23 illuminates a longitudinal section 27 of the sample medium 11 within the gap 12 between the tube 13 and the float 14, see FIG. 2. The means for positioning and rotating 26 the assembly 19 permits illumination of all radial sections of the sample medium 11 by moving the assembly 19 when the longitudinal section 27 is rotated through the line of light 23. Although not specifically shown those skilled artisans would understand how the means for positioning and rotating 26 the assembly 19 may have a motor and a driving connection to the assembly 19.

Figure 5:
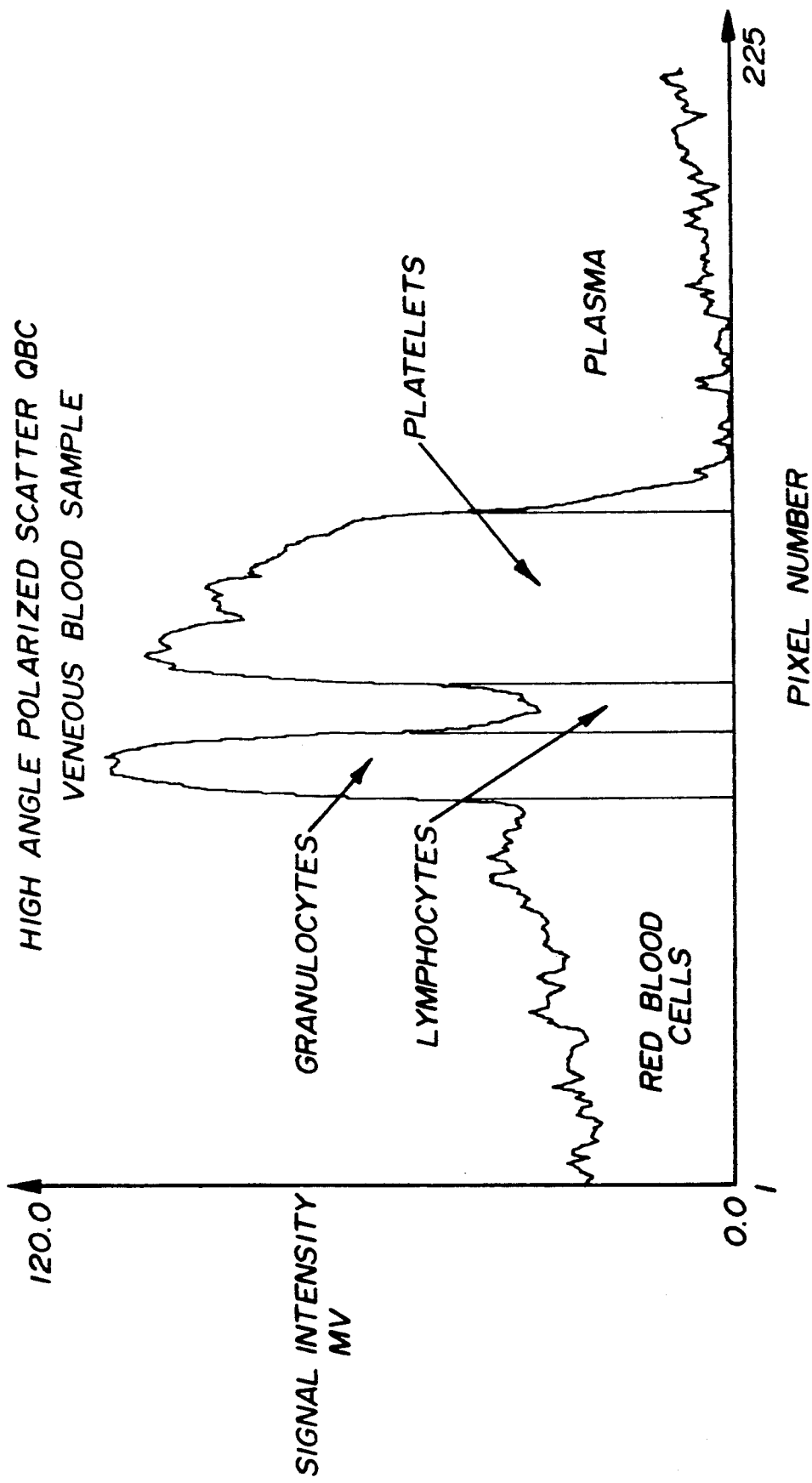
FIG. 5 is a graph with data collected for a sample medium wherein high angle scatter measurements collected by the apparatus disclosed herein is plotted against pixel number of the detector.
Figure 6:
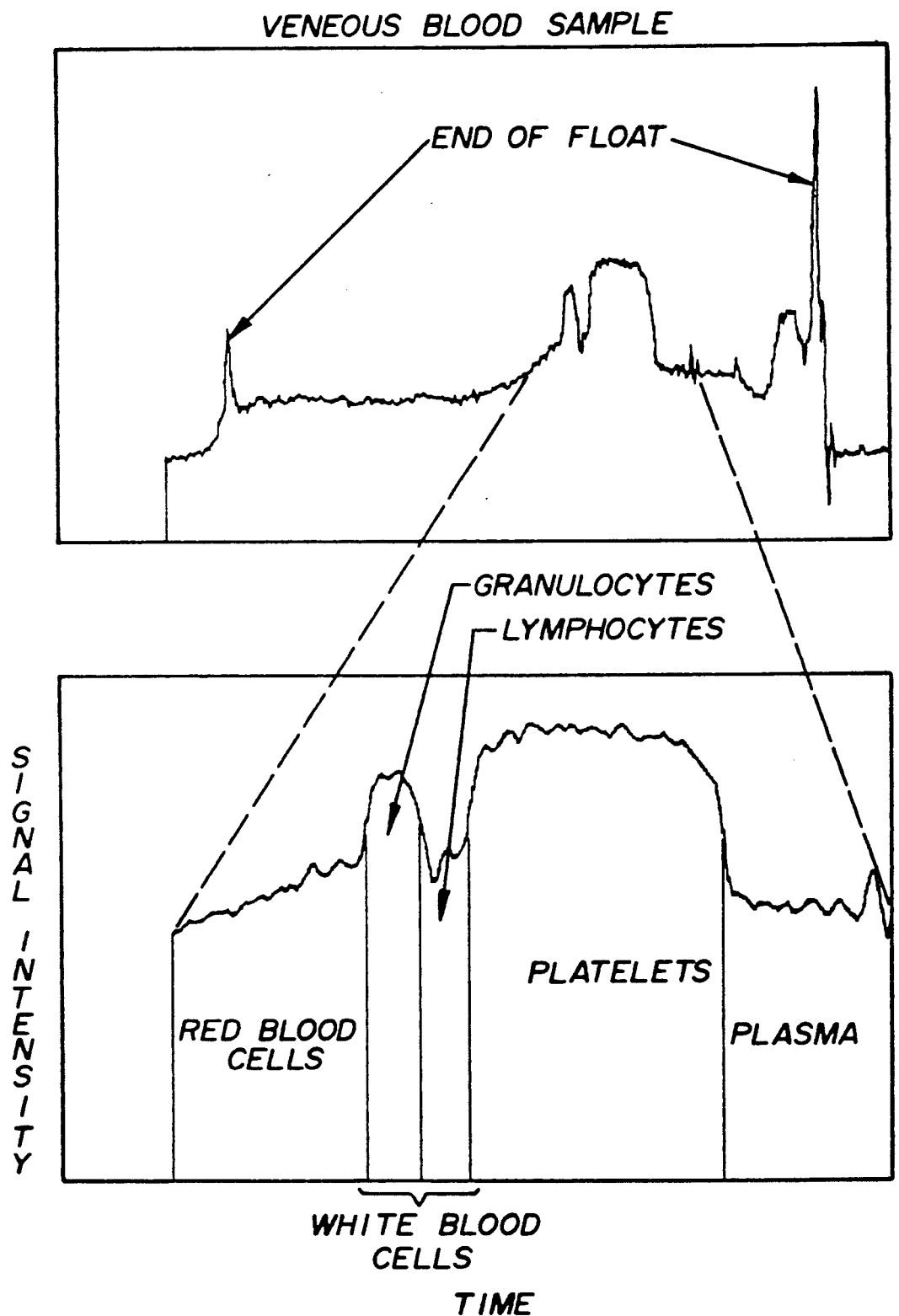
FIG. 6 is a graph and an enlarged part of that graph, each showing the data collected with a scanning beam apparatus and a single element detector in the near field. In this figure, the high angle scatter signal intensity is plotted as function of time.

A light detection means 28 is positioned normal to the optical axis A of the light source 20, parallel to the longitudinal axis C of the tube 13 and aligned to receive light affected by the longitudinal section 27 of the sample medium 11. A light filtering means 29 is shown in FIG. 1 located between the assembly 19 and the light detection means 28. The filtering means is arranged to selectively pass an optical property indicative of the nature of the sample medium 11 to be analyzed. Signal processing means 30 associated with the light detection means 28 analyzes signals therefrom. As shown in FIGS. 5 and 6 the intensity of the light detected in millevolts is plotted against pixel or time, respectively. The pixels represent positions on the light detection means such that each is a particular local or band width (axial height in FIG. 1) of the longitudinal section 23 from which light affected by the sample medium 11 was detected. Similarly, the timing of receipt of signals is plotted in FIG. 6 and represents the position of the scan by the light beam controlling means 22 relative to the longitudinal section 23 from which light affected by the sample medium 11 was detected. That is to say that the light controlling means 22 can cause the light beam 21 to illuminate the longitudinal section 23 over time. The mathematics and computer equipment used to convert the timing of the scan and thus calculate the amount (band width) of each constituent measured in the longitudinal section 23 are readily available.

The preferred light source 20 would be a laser diode or a frequency doubled laser diode which provides the light beam 21 polarized normal to the longitudinal axis C and along the optical axis A. The laser diode preferably emits light of a wavelength to cause fluorescence emissions from the sample medium 11 within the gap 12 and simultaneously emits a second wavelength in the near infra-red used to measure high angle scatter from the sample medium 11 within the gap 12. In particular, the light filter means 29 may have selectable color filters to selectively pass light of the desired fluorescent wavelength properties to the light detection means 28. Alternatively, the light filter means 29 may have selectable polarization filters to selectively pass light of the desired polarization indicative of high angle scatter properties to the light detection means 28. As shown in FIG. 3, the light detection means 28 might alternately include an imaging lens 30 to form an image of the assembly 19 on the light detection means 28 which would in this embodiment preferably be a linear detector array. The signal processing means analyzes signals by counting the number of pixels of the linear detector array. The data used to generate the plot of FIG. 5 came from just such an arrangement.

The light detection means 28 alternatively may have a single detector element shown in dash lines at 31 in FIG. 3. In that apparatus the line of light 23 is formed by scanning with the light controlling means 22 so the single detector element 31 placed in the near field of the sample medium 11 as shown in FIG. 3 provides varying intensity signals as a function of time. The data for the graph of FIG. 6 was obtain with that alternative arrangement. The signal processing means 30 analyzes signals and measures the timing of signals from the scanning illumination beam.

A method determines the optical properties of the sample medium 11 within the gap 12 of the assembly 19 of the tube 13 and cylindrical float 14 located substantially concentrically within the tube 13. The method has the steps of transmitting the polarized light beam 21 along the optical axis A at a wavelength for which the material of the tube 13 is transparent. The major axis B of polarization of the light beam 21 is positioned normal to the longitudinal axis C of the tube 13. Converting the light beam 21 to the line of light 23 in the plane 24 along the axis C of the tube 13 when the tube 13 is aligned with the optical axis A to receive the polarized beam 21 of light is another step of the preferred method. The step of rotating and positioning the assembly 19 of the tube 13 and the cylindrical float 14 within the plane 24 of the line of light 23 so that the line of light 23 is parallel to the longitudinal axis C of the assembly 19 and is displaced laterally from the longitudinal axis C thereof illuminates a longitudinal section 27 of the sample medium within the gap 12 between the tube 13 and the float 14. All radial sections of the sample medium would be illuminated over a period of time by the step of rotating the assembly 19 about its axis C and within the line of light 23.

The next step detects with the light detection means 28 by positioning the light detection means normal to the optical axis A of the light beam 21 and parallel to the longitudinal axis C of the tube 13. The light detection means 28 is, in the next step of the method, aligned to receive the light effected by the optical properties of the sample medium 11. The steps of filtering the light effected to selectively pass light indicative of the nature of the sample medium 11 being analyzed with the light detection means and signalling the nature of the sample medium 11 as a function of the effected light are preferably followed.

Figure 4:
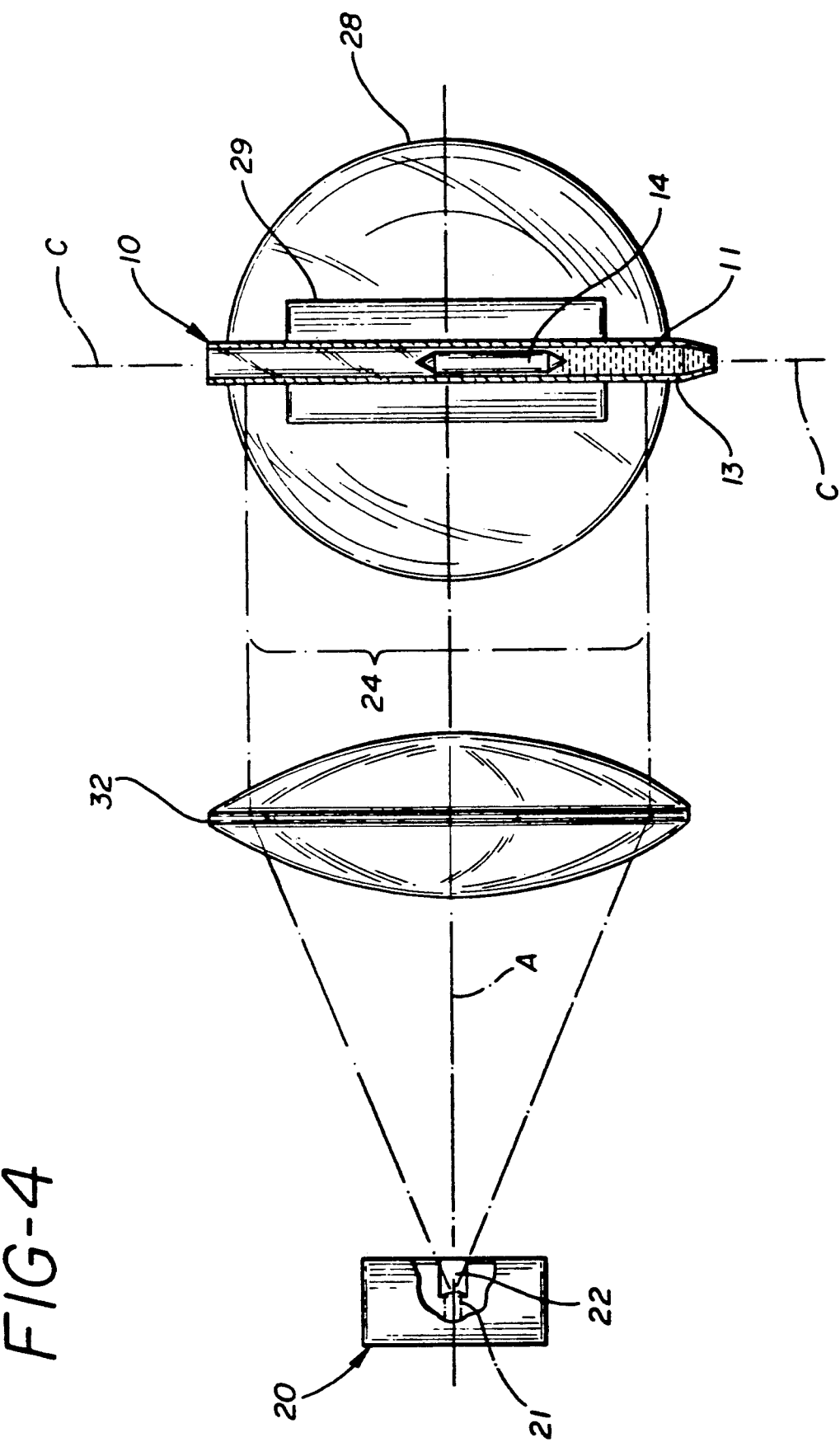
FIG. 4 is a side view of an optical layout which illuminates the gap between the float and tube for analysis of a sample medium within the gap.
Figure 7:
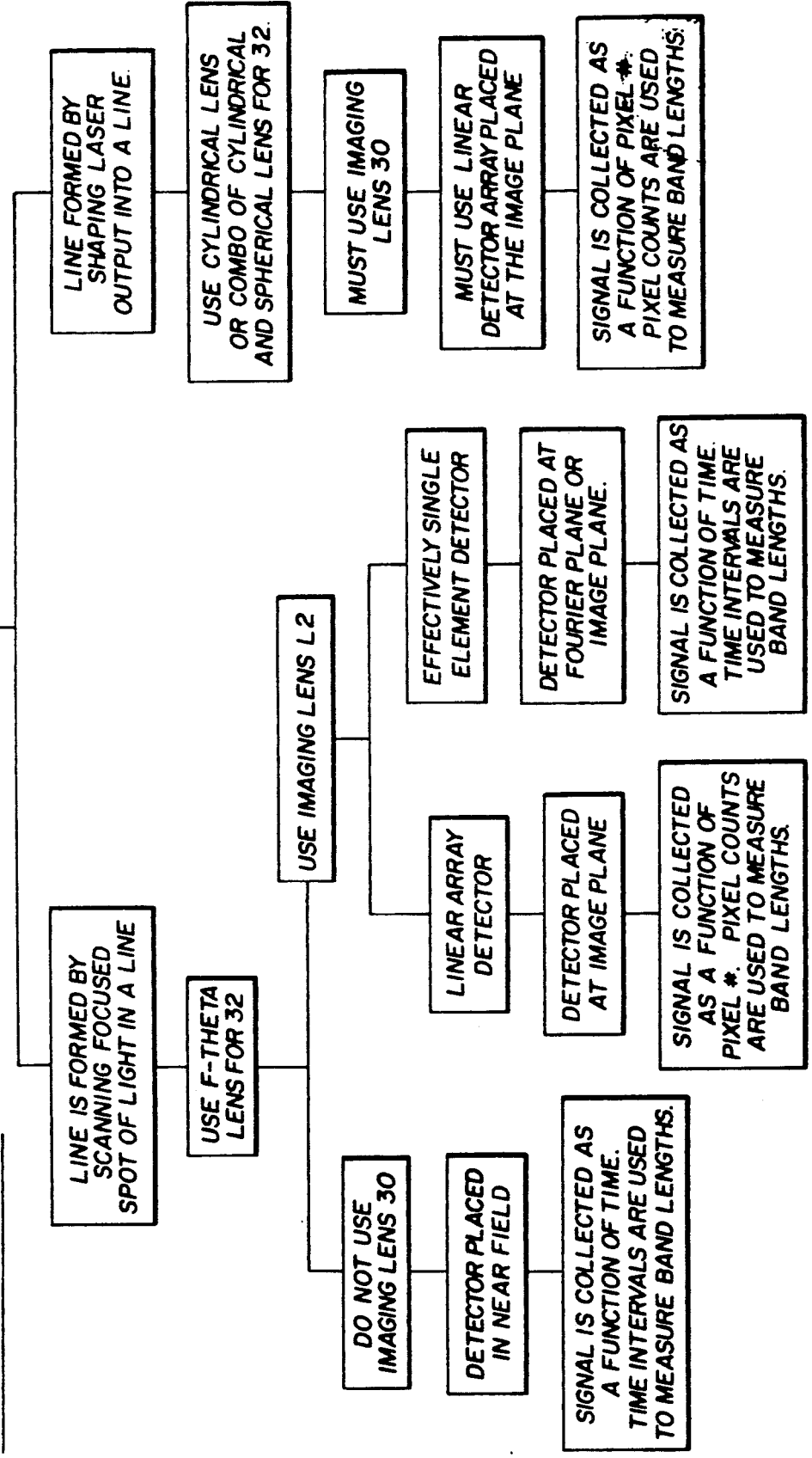
FIG. 7 is chart listing various alternate optical layout options for the apparatus and method used to illuminate and detect the high angle scatter and/or fluorescence from the sample medium within the gap between the float and tube.

The chart in FIG. 7 relates to various embodiments shown in the FIGS. 1-4. In particular, every one of the possible combinations includes the illumination of a QBC ® tube with a line of light parallel to the tube axis and positioned so that the illumination is of the gap between the tube 13 and the float 14. The illumination is with light that is polarized normal to the tube axis C as explained herein. Two techniques may be used to control the light used for illumination. One technique includes forming the light by scanning a focused spot of light along the line 23. This is shown in FIGS. 1, 3 and 4 in a general way since skilled artisans will know how to generate the line 23 of light by scanning. Another approach is to form a line of light by shaping the laser beam output into the line 23 as shown in FIGS. 1, 3 and 4. With either technique to convert the light to a line 23 a lens 32 may be positioned between the laser 20 and the QBC ® product 10. The lens 32 may be a F-theta lens or a cylindrical lens depending upon whether the line 23 of light is formed by scanning or by shaping respectively. As shown in the chart of FIG. 7 when the scanning technique is used, there are two approaches for analyzing light which has been influenced by sample medium 11 in the QBC ® product 10. Imaging lens 30 may be used either with a linear array or a single element detector 28 positioned as shown in FIG. 3. Signals may be detected and collected as a function of the pixel number or over a period of time as heretofore explained. The detector 28 will be placed at the image plane when the linear detector array is used and will be placed at the fourier or image plane if the single element detector is used.

An alternative for line of light 23 formed by scanning requires no imaging lens 30. The detector 31 is placed in the near field such that signals can be collected as a function of time and time intervals may be used to measure the band lengths of sample medium 11 in a QBC ® product 10.

What is claimed is:

1. An apparatus to determine the optical properties of a sample medium within a gap in an assembly of a transparent tube and cylindrical float located substantially concentrically within the tube comprising:
   a monochromatic or bichromatic light source providing a polarized light beam along an optical axis at a wavelength for which the materials of the tube are transparent and the major axis of polarization of the light beam is normal to the longitudinal axis of the tube;
   a light beam controlling means for converting the light beam to a line of light in a plane positioned along an axis of the tube, the tube aligned with the optical axis to receive the polarized light beam;
   means for positioning and rotating the assembly of the tube and the cylindrical float within the plane with the line of light parallel to the longitudinal axis of the assembly and displaced laterally from the longitudinal axis of the tube to illuminate a longitudinal section of the sample medium within the gap between the tube and the float, the means for positioning and rotating the assembly capable of illuminating all radial sections of the sample medium;
   a light detection means positioned normal to the optical axis of the light source, parallel to the longitudinal axis of the tube and aligned to receive light passing through the longitudinal section of the sample medium;
   a light filtering means located between the tube and the light detection means, the light filtering means arranged to selectively pass an optical property indicative of the nature of the sample medium to be analyzed, and
   signal processing means associated with the detector for analyzing signals therefrom.

2. The apparatus of claim 1 where the light source is a laser diode or frequency doubled laser diode providing the light beam polarized normal to the longitudinal axis and along the optical axis.

3. The apparatus of claim 2 wherein the laser diode emits light of a wavelength to cause fluorescence emissions from the medium within the tube.

4. The apparatus of claim 1 wherein the light filter means includes selectable polarization filters to selectively pass light of the desired polarization for high angle scatter properties to the light detecting means.

5. The apparatus of claim wherein the light filter means includes selectable color filters to selectively pass light of the desired fluorescent wavelength properties to the light detecting means.

6. The apparatus of claim 1 wherein the light detecting means includes an imaging lens to form an image of the tube on a detector thereof.

7. The apparatus of claim 6 wherein the detector is a linear detector array.

8. The apparatus of claim 7 wherein the signal processing means analyzes signals by counting the number of pixels of the linear detector array.

9. The apparatus of claim 6 wherein the detector is a single detector element.

10. The apparatus of claim 9 wherein the signal processing means analyzes the signals measuring the timing of signals with the scanning illumination beam and single element detector.

11. The apparatus of claim 1 wherein the illumination line is formed by scanning means and the light detecting means includes a single detector element placed in the near field of the sample medium.

12. The apparatus of claim 11 wherein the signal processing means analyzes the signals measuring the timing of signals with the scanning illumination beam and single element detector.

13. A method for determining the optical properties of a sample medium within a gap of an assembly of a tube and cylindrical float located substantially concentrically within the tube having the following steps:
   transmitting a polarized monochromatic or bichromatic light beam along an optical axis at a wavelength for which the material of the tube is transparent and wherein the major axis of polarization of the light beam is positioned normal to the longitudinal axis of the tube;
   converting the light beam to a line of light in a plane along the axis of the tube when the tube is aligned with the optical axis to receive the polarized beam of light;
   rotating and positioning an assembly of the tube and the cylindrical float within the plane of the line of light with the line of light parallel to the longitudinal axis of the assembly and displaced laterally from the longitudinal axis thereof to illuminate a longitudinal section of the sample medium within the gap between the tube and the float;

illuminating all radial sections of the sample medium over a period of time by rotating the assembly about its axis and within the line of light;

detecting with a light detection means positioned normal to the optical axis of the light beam and parallel to the longitudinal axis of the tube, the light detection means aligned to receive the light effected by the optical properties of the sample medium;

filtering the light effected to selectively pass light indicative of the nature of the sample medium being analyzed with the light detection means, and signalling the nature of the sample medium as a function of the effected light.

* * * * *